(12) United States Patent
Garber et al.

(10) Patent No.: US 9,915,582 B2
(45) Date of Patent: Mar. 13, 2018

(54) MODULAR PRESSURE TESTING UNIT

(71) Applicant: Offshore Energy Services, Inc., Houma, LA (US)

(72) Inventors: Gary Russell Garber, Houma, LA (US); Kevin Michael Guidry, Houma, LA (US); Dennis Penisson, Houma, LA (US); Kirk Pepper, Houma, LA (US)

(73) Assignee: Offshore Energy Services, Inc., Houma, LA (US)

( * ) Notice: Subject to any disclaimer, the term of this patent is extended or adjusted under 35 U.S.C. 154(b) by 705 days.

(21) Appl. No.: 14/506,135

(22) Filed: Oct. 3, 2014

(65) Prior Publication Data

US 2016/0097271 A1   Apr. 7, 2016

(51) Int. Cl.
| | |
|---|---|
| *G01M 3/02* | (2006.01) |
| *G01M 3/32* | (2006.01) |
| *E21B 41/00* | (2006.01) |
| *G01M 3/36* | (2006.01) |
| *G01N 3/12* | (2006.01) |

(52) U.S. Cl.
CPC ........... *G01M 3/3281* (2013.01); *E21B 41/00* (2013.01); *G01M 3/363* (2013.01); *G01N 3/12* (2013.01)

(58) Field of Classification Search
CPC .............................. G01N 3/313; G01M 3/3281
See application file for complete search history.

(56) References Cited

U.S. PATENT DOCUMENTS

| | | | |
|---|---|---|---|
| 3,827,282 A | 8/1974 | Brister | |
| 4,016,951 A | 4/1977 | Dick et al. | |
| 4,081,990 A | 4/1978 | Chatagnier | |
| 4,342,402 A * | 8/1982 | Jungles | B65F 1/16 220/848 |
| 4,416,147 A | 11/1983 | Hasha | |
| 4,470,295 A | 9/1984 | Pounds et al. | |
| 4,508,237 A * | 4/1985 | Kreeger | B65D 11/182 206/509 |
| 4,522,258 A | 6/1985 | DeWald | |
| 4,548,069 A | 10/1985 | Nousak | |
| 4,599,829 A * | 7/1986 | DiMartino, Sr. | E04B 1/3483 410/79 |

(Continued)

FOREIGN PATENT DOCUMENTS

GB           2512981 A  * 10/2014   ............... E04H 5/04

OTHER PUBLICATIONS

GB—2512981.*

*Primary Examiner* — Harshad R Patel
*Assistant Examiner* — Tran M Tran
(74) *Attorney, Agent, or Firm* — Jones Walker LLP

(57) ABSTRACT

A pressure testing unit for pressure testing equipment including a test cell having first and second side walls, a cell frame, a lid pivotally mounted on the first side wall, a first tie rod disposed through the cell frame, a second tie rod disposed through the cell frame, a first impact plate removably secured to proximal ends of the first and second side walls and proximal ends of the first and second tie rods, and a second impact plate removably secured to distal ends of the first and second side walls and distal ends of the first and second tie rods. The test cell may be lengthened by attaching a second test cell thereto. One of the impact plates may be removed from the test cell, and receptacles on the test cell may be connected to receptacles on the second test cell.

21 Claims, 11 Drawing Sheets

(56) References Cited

U.S. PATENT DOCUMENTS

| | | | |
|---|---|---|---|
| 4,727,749 A | 3/1988 | Miller et al. | |
| 4,766,934 A | 8/1988 | Ollivaud et al. | |
| 4,836,395 A * | 6/1989 | Goutille | B65D 88/121 220/1.5 |
| 4,879,896 A | 11/1989 | Miller et al. | |
| 4,955,501 A * | 9/1990 | Hodge | B65F 1/1615 220/315 |
| 5,044,252 A | 9/1991 | Gamadi et al. | |
| 5,571,043 A | 11/1996 | Lyras et al. | |
| 5,678,715 A * | 10/1997 | Sjostedt | B65D 88/121 220/1.5 |
| 5,761,854 A * | 6/1998 | Johnson | B60P 3/34 135/116 |
| 5,765,707 A * | 6/1998 | Kenevan | B65D 11/18 220/4.28 |
| 5,884,569 A | 3/1999 | Donovan | |
| 6,073,943 A * | 6/2000 | Serrault | B65F 1/02 280/30 |
| 6,216,751 B1 * | 4/2001 | Trpkovski | E06B 3/6775 141/129 |
| 6,367,391 B1 * | 4/2002 | Thoman | B29C 70/086 105/404 |
| 6,439,120 B1 | 8/2002 | Bureaux et al. | |
| 6,591,201 B1 | 7/2003 | Hyde | |
| 6,593,136 B1 * | 7/2003 | Geiss | C12M 23/44 435/243 |
| 6,874,401 B2 | 4/2005 | Bishop et al. | |
| 7,023,339 B2 | 4/2006 | Stomski | |
| 7,056,081 B2 * | 6/2006 | Kelly | B65D 88/022 220/1.5 |
| 7,083,369 B2 * | 8/2006 | Nyeboer | B65D 19/12 410/43 |
| 7,096,718 B2 * | 8/2006 | Matzner | G01N 3/12 73/37 |
| 7,204,183 B2 | 4/2007 | Cirillo | |
| 7,237,993 B2 * | 7/2007 | Farley | B65D 19/44 410/43 |
| 7,712,405 B2 * | 5/2010 | Toycen | F42D 5/045 86/50 |
| 7,753,090 B2 | 7/2010 | Earp | |
| 7,946,149 B1 * | 5/2011 | Knight | G01L 5/14 73/12.08 |
| 8,123,061 B1 * | 2/2012 | Brown | B65F 1/02 220/4.28 |
| 8,230,747 B2 | 7/2012 | Lindeberg | |
| 8,240,499 B2 * | 8/2012 | Lu | B65F 1/163 220/263 |
| 8,256,270 B2 | 9/2012 | Fielding et al. | |
| 8,360,708 B2 * | 1/2013 | Mashburn | B65G 1/0442 211/208 |
| 8,382,033 B2 * | 2/2013 | Reece | B64C 1/066 220/1.5 |
| 8,556,112 B2 * | 10/2013 | Tujague, Sr. | B65D 88/526 108/26 |
| 8,763,672 B2 * | 7/2014 | Smart | E05F 15/605 160/188 |
| 9,057,180 B1 * | 6/2015 | Sewell | B65D 55/00 |
| 9,290,300 B2 * | 3/2016 | Hendrickson | B65D 23/00 |
| 9,382,768 B2 * | 7/2016 | Garber | E21B 19/166 |
| 9,410,874 B2 * | 8/2016 | He | G01N 3/313 |
| 9,487,352 B2 * | 11/2016 | Fenton | B65D 88/121 |
| 9,567,159 B2 * | 2/2017 | Loney | B65F 1/1468 |
| 2004/0107823 A1 * | 6/2004 | Kiley | B65D 88/14 86/50 |
| 2005/0237178 A1 | 10/2005 | Stomski | |
| 2005/0269079 A1 | 12/2005 | Franklin | |
| 2008/0223857 A1 | 9/2008 | Palley et al. | |
| 2009/0193877 A1 | 8/2009 | Fielding et al. | |
| 2009/0211364 A1 | 8/2009 | Lindeberg | |
| 2011/0192548 A1 | 8/2011 | Dupray et al. | |
| 2012/0312147 A1 | 12/2012 | Abbe et al. | |

* cited by examiner

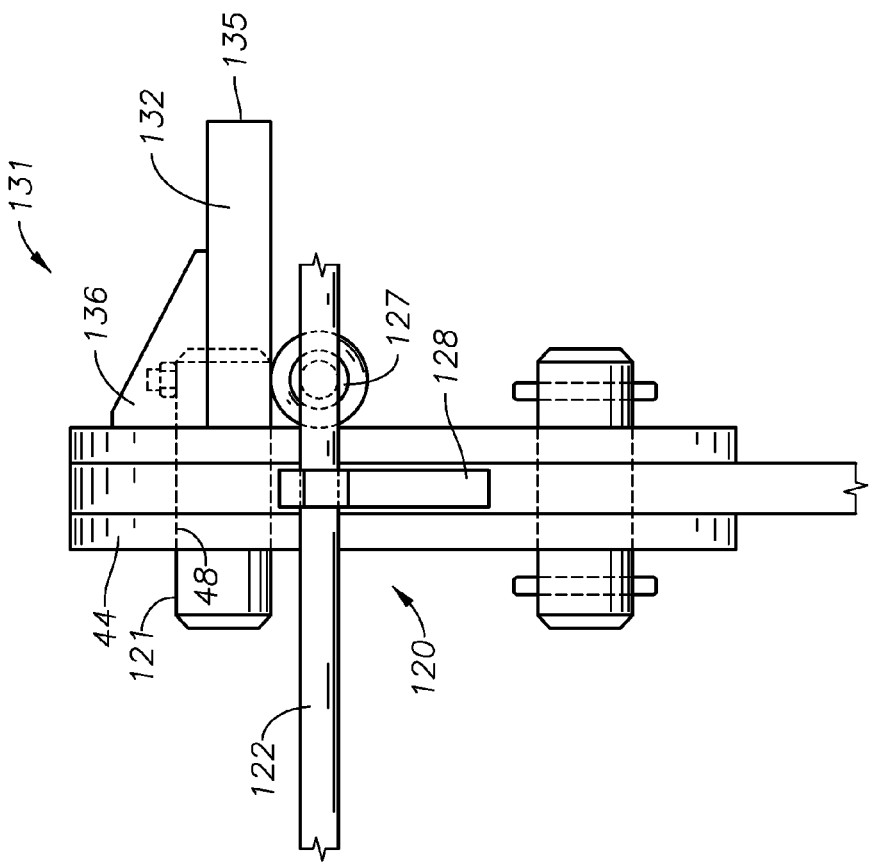
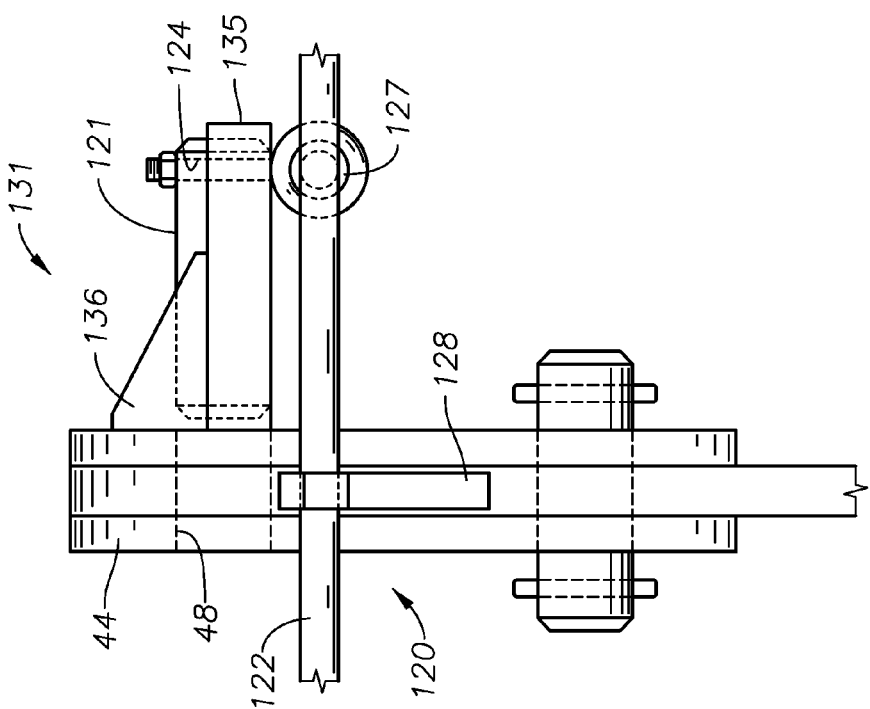
FIG. 5B
FIG. 5A

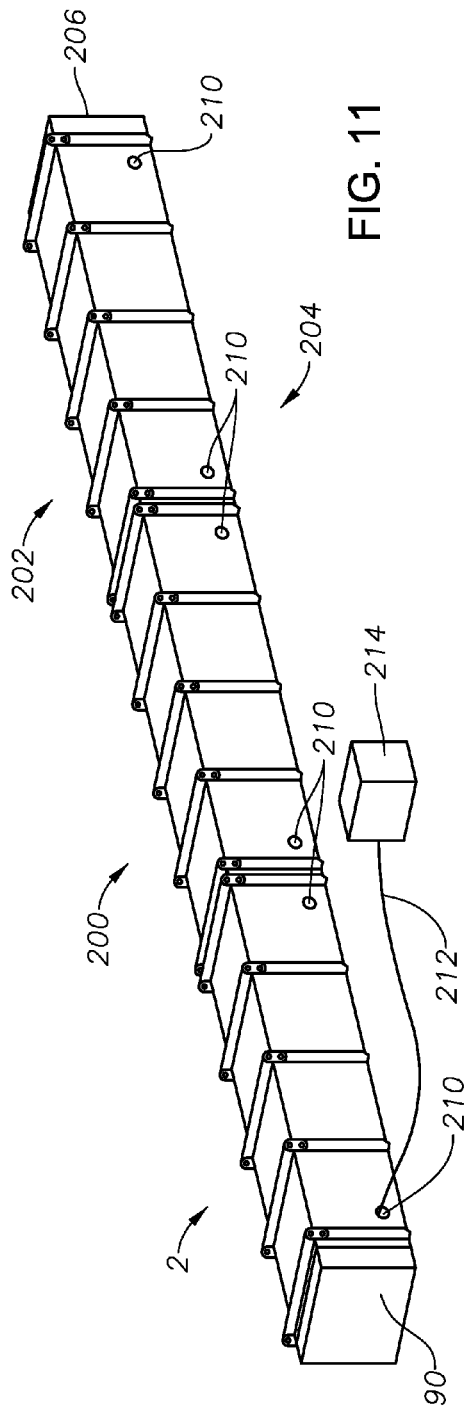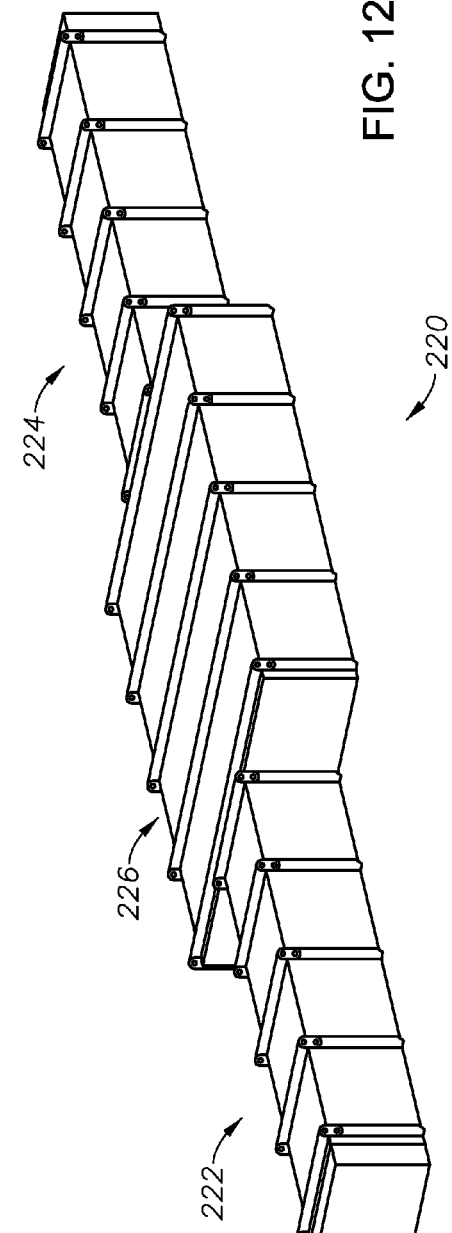

MODULAR PRESSURE TESTING UNIT

BACKGROUND OF THE INVENTION

This invention relates to a pressure test cell. More particularly, but not by way of limitation, this invention relates to a portable test cell for pressure testing equipment used in the oil and gas industry.

Operators search for hydrocarbon reservoirs in most areas of the world, including remote and hostile areas. Hydrocarbon reservoirs are generally under significant pressure and temperature environments. In the exploration, drilling, and production phases, operators must perform work under conditions that require extreme caution. If a failure occurs on equipment used while exploring, drilling, or producing, a blow-out may ensue that may result in loss of life and significant property damage. Operators find it advisable to pressure test equipment in order to ensure that the equipment contains the necessary structural integrity as well as sealing means. As well understood by those of ordinary skill in the art, governments and regulatory agencies have enacted rules that require pressure testing equipment.

Failures may occur during pressure testing. Hence, there is need to protect people and equipment at the testing site.

BRIEF DESCRIPTION OF THE DRAWINGS

FIG. 5A is a side view of the locking pin system with the locking pin in an unlatched position.

FIG. 5B is a side view of the locking pin system with the locking pin in a latched position

FIG. 11 is a schematic of a plurality of test cells with portals and monitoring equipment.

FIG. 12 is a schematic of a plurality of test cells having varying sizes.

DETAILED DESCRIPTION OF THE PREFERRED EMBODIMENTS

Figure 1:
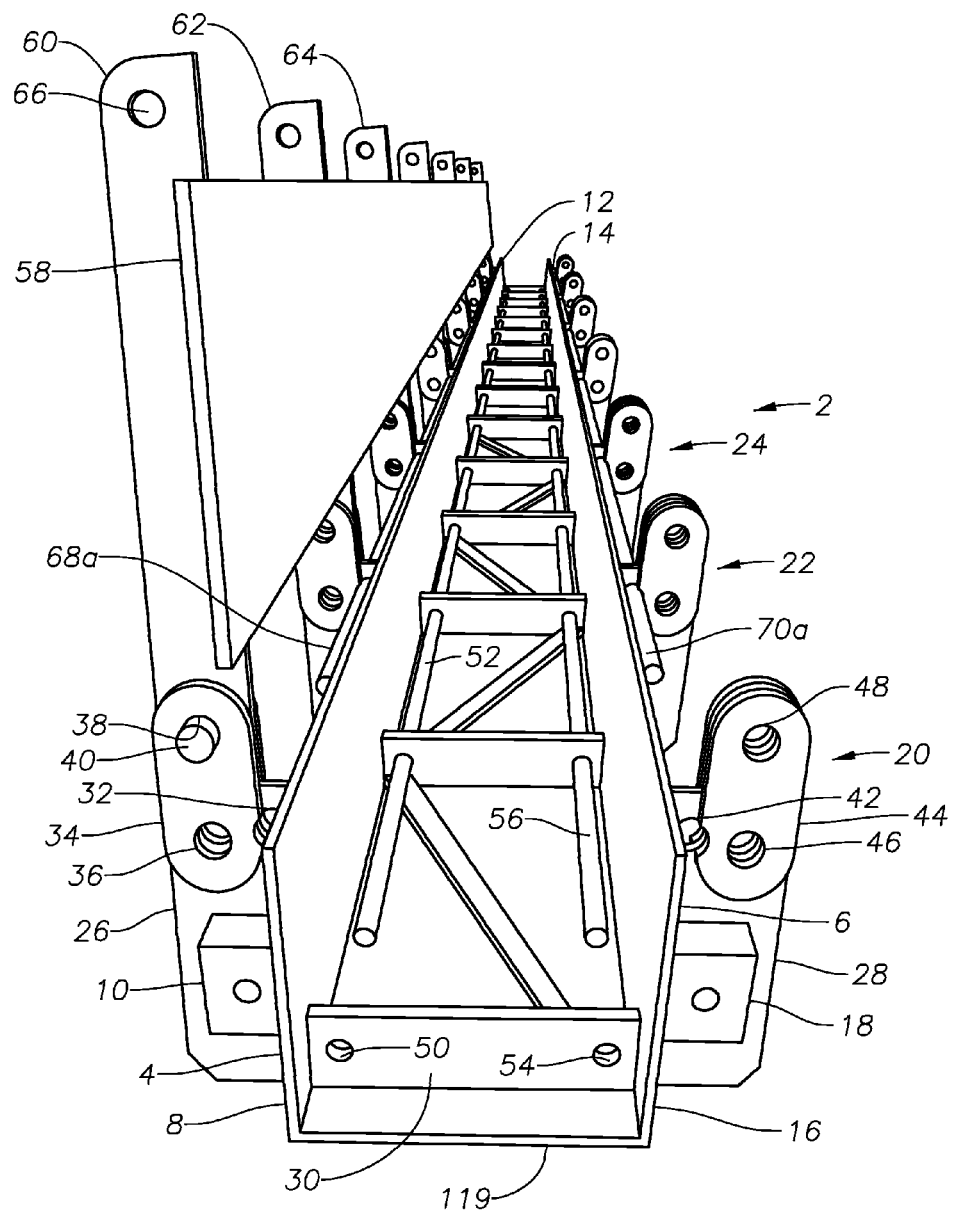
FIG. 1 is a perspective front view of a test cell with the lid open.

FIG. 1 is a perspective front view of one embodiment of the test cell 2. In this embodiment, the test cell 2 is generally the shape of a rectangular box. More specifically, the partial view of FIG. 1 depicts the first side wall 4 and the second wall side 6, wherein the sides 4 and 6 are generally vertically upstanding walls. The side wall 4 will have an end 8 that will contain a receptacle 10 and an end 12 that will also contain a receptacle (not seen here). The side wall 6 will have an end 14 that will contain a receptacle (not seen here) and an end 16 that will also contain a receptacle 18. The receptacles 10 and 18 may be referred to as mating block members 10 and 18.

FIG. 1 also depicts multiple cell frames, for instance cell frames 20, 22, 24. The cell frame 20 includes a first vertical post 26, a second vertical post 28 and a bottom horizontal brace 30. In one embodiment, the brace 30 is formed in one piece with the posts 26, 28. In another embodiment, the posts and brace may be attached via welding. The horizontal brace 30 is fitted through slots on the walls 4, 6. The vertical post 26 contains an opening 32 for a tie rod that is described below. A frame link 34 is attached to the vertical post 26, wherein the frame link 34 is attached via welding in one embodiment. The frame link 34 contains opening 36 for a pin (not shown) and the opening 38 for a pin member 40. In one embodiment, vertical locking members may be secured on either end of pin member 40 after being positioned in opening 38 in order to prevent pin member 40 from slipping out of opening 38. The vertical post 28 is of similar construction, wherein the vertical post 28 contains an opening 42 for a tie rod. Also, the frame link 44 is attached, such as by welding, to the vertical post 28. The frame link 44 contains the opening 46 for a removable pin (not shown) and the opening 48 for a selectively removable pin (not seen here). The horizontal brace 30 contains an opening 50 for a tie rod 52, and an opening 54 for a tie rod 56. The other cell frames are of similar design.

FIG. 1 depicts the lid 58 which will pivot from an open position to a closed position. The lid 58 will have lid beams attached, such as by welding, to the top portion of the lid 58. For instance, FIG. 1 depicts the lid beams 60, 62, 64, wherein the lid beams 60, 62, 64 will each contain an opening, such as opening 66 that will cooperate with the opening 48 on the frame link 44 for placement of a pin there through for securing the lid 58 in the closed position.

FIG. 1 depicts the tie rods 52, 56 as well as the tie rods 68a, 70a. The tie rod 68a will cooperate with the openings in the vertical post, such as opening 32 and the tie rod 70a will cooperate with the opening 42. While the individual tie rods will be of fixed length, the tie rods can extend several test cells, and wherein the tie rods would be extended with the use of a coupler (not shown here) that is described below.

Figure 2:
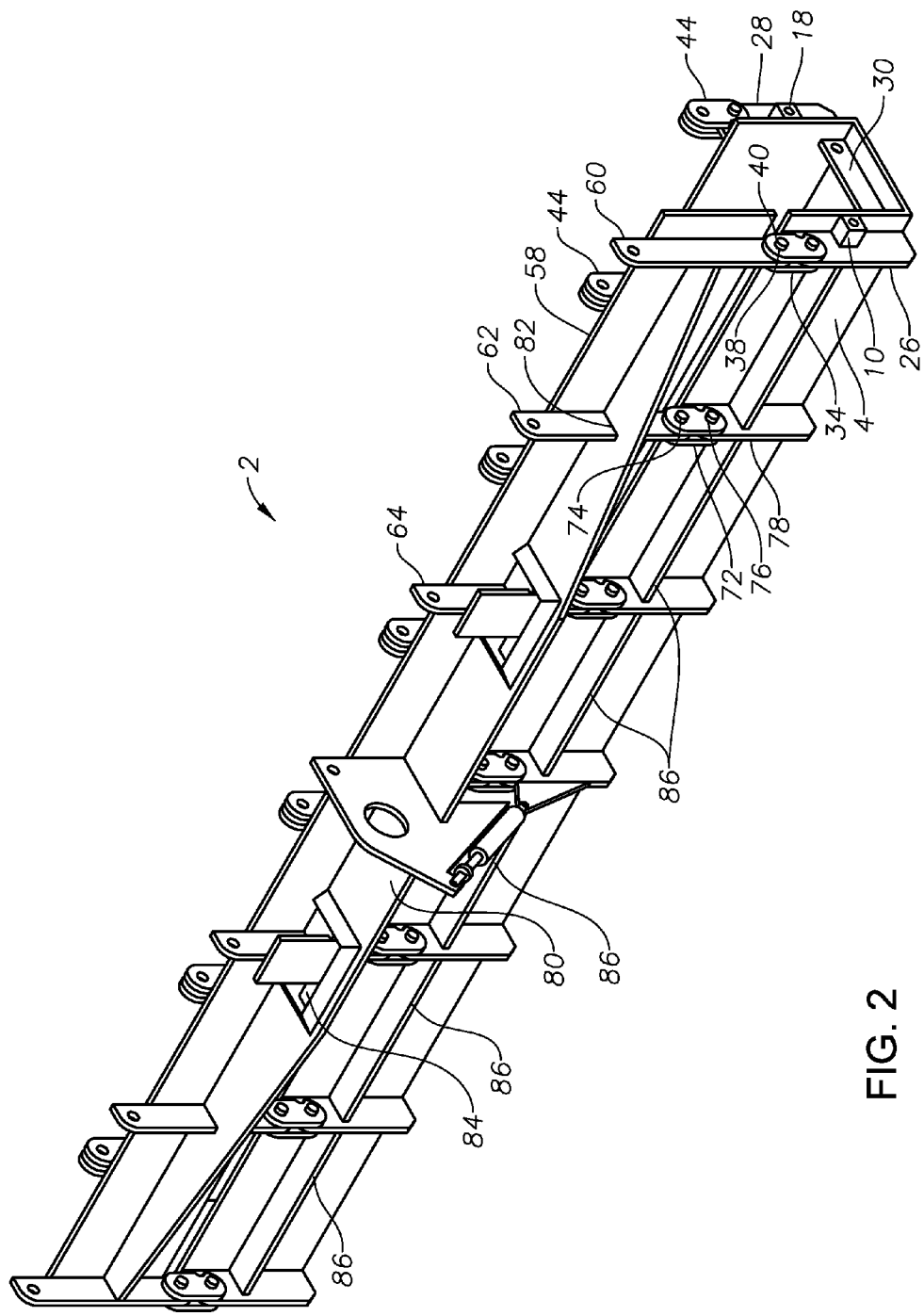
FIG. 2 is a perspective side view of the test cell.

Referring now to FIG. 2, test cell 2 includes multiple lid beams, such as lid beams 60, 62, 64, which may be attached to the lid 58 via welding. It should be noted that like numbers appearing in the various figures refer to like components. The lid beams (such as lid beams 60, 62, 64) are pivotally mounted to the vertical post, and in particular to the frame links. FIG. 2 depicts the lid beam 60 being pivotally mounted to the frame link 34 via the pin 40 being inserted through the opening 38. FIG. 2 also depicts the frame link 72 having the pin 74 inserted through the opening 76, and wherein the frame link 72 extends from vertical post 78. Hence, the lid 58 can be pivotally opened and closed.

FIG. 2 also depicts the spar 80, wherein the spar 80 is generally a structural plate member that extends vertically from the lid 58. The spar 80 will have slots, such as slot 82, that will allow for entry of the lid beams, such as lid beam 62. The lid beam 62 can be welded into the slot 82 to attach the lid beam 62 to the spar 80 and lid 58. The spar 80 will also contain lifting receptacles, such as opening 84, that can accommodate lifting devices such as fork lift prongs or slings from cranes for movement of the test cell 2. Alternate embodiments of test cell 2 may include other lifting receptacles for facilitating lifting of test cell 2. For example, the lifting receptacle may include one or more pad eyes disposed on lid 58, the lid beams, or spar 80.

FIG. 2 also depicts the receptacles, including the receptacles 10, 18. More specifically, the side wall 4 contains the receptacle 10, wherein the receptacles shown here comprise mating blocks that will allow connection between two individual test cells (e.g., test cell 2), as will be more fully explained later. In another embodiment, the side walls 4 and 6 may contain receptacles, wherein in this embodiment the receptacles comprise prongs (i.e. forks) that will allow insertion of a cooperating element of another test cell. The vertical post 26, bottom horizontal brace 30 and the vertical post 28 are depicted in FIG. 2 (which together may be referred to as a cell frame), and wherein the vertical post 26 will contain the frame link 34 and the vertical post 28 will contain the frame link 44. In one embodiment, test cell 2 may further include horizontal support beams 86 affixed to side wall 4 and horizontal support beams affixed to side wall 6 (not visible here). The horizontal support beams 86 may provide additional structural support to side walls 4 and 6 in the event of an equipment failure during pressure testing operations. In an alternate embodiment, test cell 2 may include no horizontal support beams.

Figure 3A:
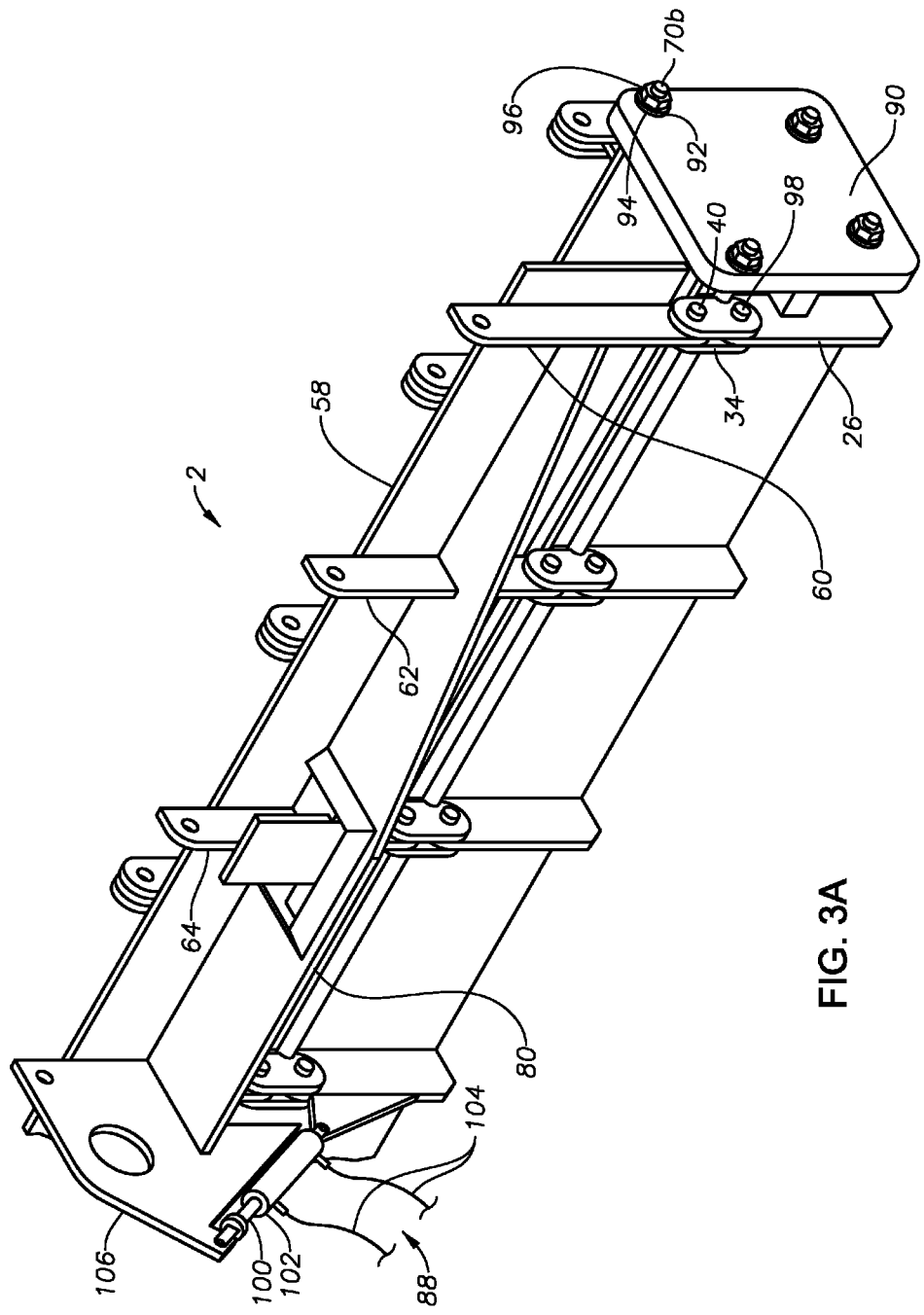
FIG. 3A is a perspective partial side view of the test cell.

Referring now to FIG. 3A, the test cell 2 of FIG. 1 may include opening member 88 and impact plate 90. The impact plate 90 will have apertures therein, such as aperture 92 that will have disposed therein the tie rod 70b (which is an extension from tie rod 70a). A washer 94 and nut 96 are included for attaching the impact plate 90 to the test cell 2. FIG. 3A shows that the tie rods extend through the vertical post, such as vertical post 26. The pin 40 is shown operatively associated with the lid beam 60 for pivoting, as previously mentioned. Also shown is the pin 98 which is fitted through the frame link 34 for providing further strength to the test cell. The opening member 88 allows for opening and closing the lid 58. The opening member 88 may be hydraulically controlled, wherein a hydraulic piston 100 extends from a hydraulic cylinder 102, with the hydraulic lines 104 linked to a control panel (not seen here) for extending and retracting the piston 100 in order to open and close the lid 58. FIG. 3A also depicts the attachment plate 106 (also referred to as arm 106), wherein the attachment plate 106 is attached to the piston 100, and the attachment plate 106 is also attached to the lid 58 so that the lid 58 may be pivoted open and closed.

Figure 3B:
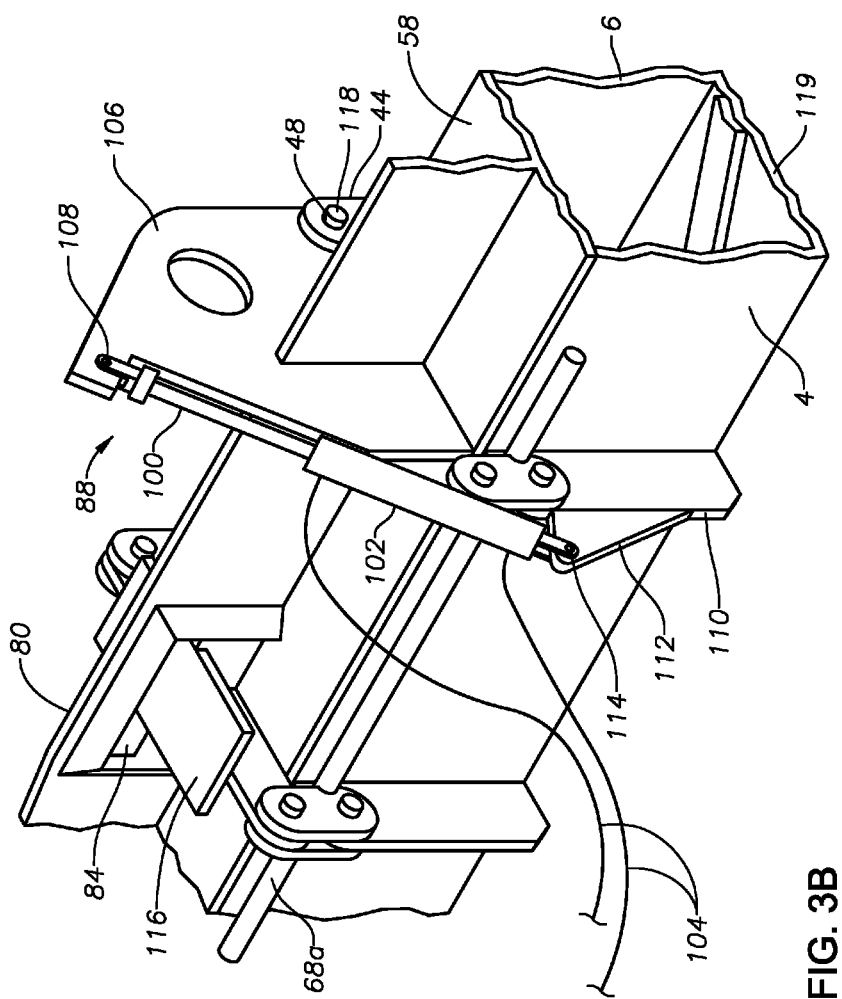
FIG. 3B is another perspective partial side view of the test cell.

FIG. 3B shows opening member 88 with lid 58 in a closed position. The opening member 88 includes the hydraulic piston 100 extending from the hydraulic cylinder 102, along with the hydraulic lines 104 that provide the hydraulic fluid as well understood by those of ordinary skill in the art. Hydraulic pistons and cylinders are commercially available, such as those manufactured by Chief Hydraulics. The piston 100 will be connected to the arm 106 at connection point pin 108, and the cylinder 102 is connected to the vertical post 110 via the attachment plate 112 at the connection point pin 114. As seen in FIG. 3B, the arm 106 is attached (via welding in one embodiment) to the spar 80. FIG. 3B depicts a lifting receptacle in the form of opening 84 in spar 80 for engaging lifting equipment, such as member 116 or a fork lift prong. FIG. 3B also depicts pin member 118 disposed through opening 48 in frame link 44. An analogous pin member is disposed through an opening in the frame link of each other cell frame. In this configuration, the pin members secure lid 58 in the closed position.

FIG. 3B also shows floor structure 119 may connect side walls 4, 6 at the base of test cell 2. Floor structure 119 may provide for a collection floor to collect fluids, such as water and hydraulic oil, from equipment during testing operations as well as providing for structural support of the bottom end of test cells. Horizontal and diagonal braces may also be used for structural support of the bottom portion of the individual test cells. In an alternative embodiment, a test cell may include horizontal or diagonal braces without floor structure 119 to allow for additional venting.

Figure 4:
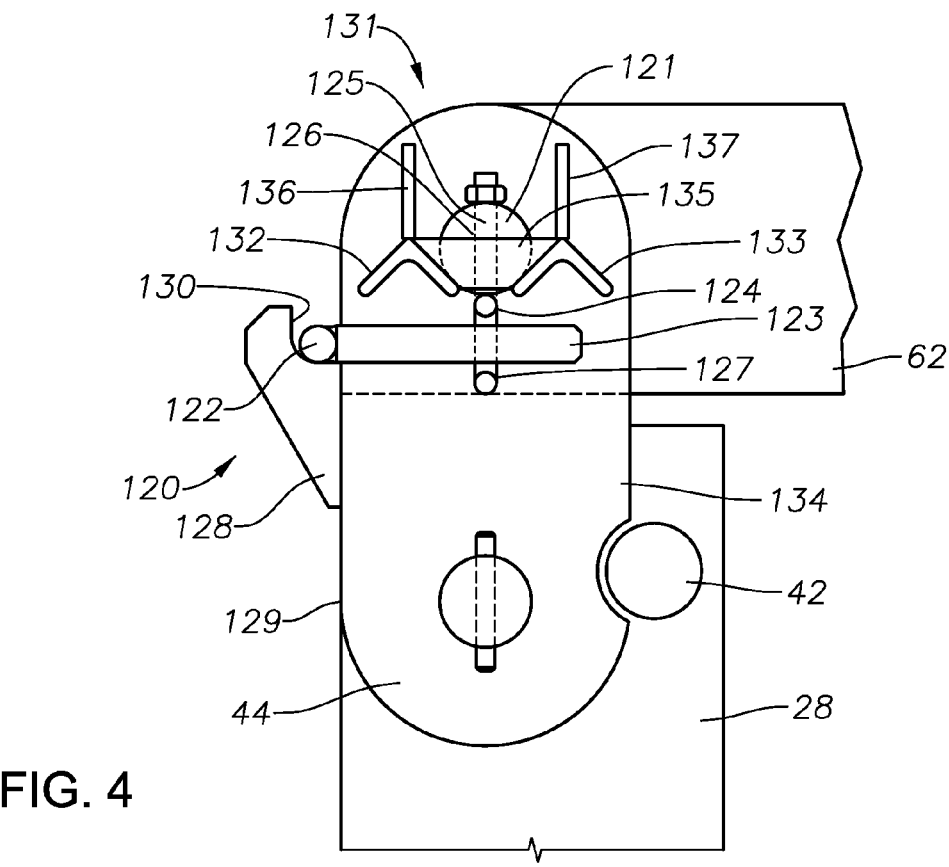
FIG. 4 is a rear view of a locking pin system of an alternate embodiment of the test cell.
Figure 6:
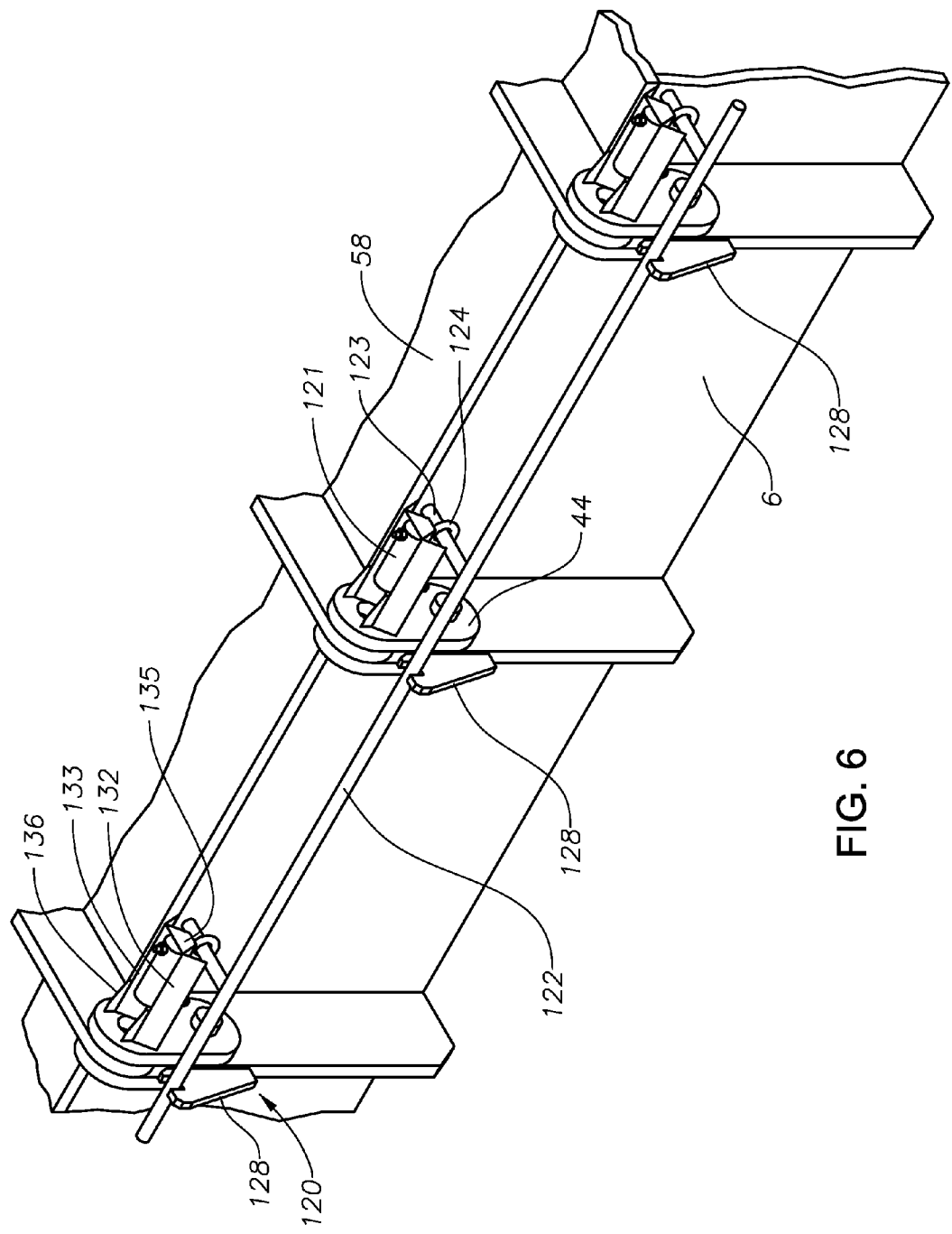
FIG. 6 is an isometric view of the test cell having the locking pin system.

FIGS. 4-6 illustrate an alternate embodiment of the test cell having locking pin system 120 configured to simultaneously engage a plurality of locking pins 121 into corresponding openings in frame links (e.g., opening 48 in frame link 44) by actuating guide rod 122 in order to more quickly secure lid 58 in the closed position. Each locking pin 121 may be operatively connected to guide rod 122 through transverse member 123 and connection member 124. In this embodiment, connection member 124 may be formed of an eye bolt having shaft portion 125 secured through bore 126 in locking pin 121 and opening 127 dimensioned to receive transverse member 123. Horizontal movement of guide rod 122 and transverse member 123 may apply a horizontal force on the eye bolt which may, in turn, cause locking pin 121 to move in the same horizontal direction as guide rod 122. In this way, horizontal movement of guide rod 122 may move locking pin 121 between an unlatched position (shown in FIG. 5A) and a latched position (shown in FIG. 5B).

Locking pin system 120 may include guide rod support 128 extending from side surface 129 of frame link 44 on second vertical post 28. Guide rod 122 may slide upon arched surface 130 of guide rod support 128. Arched surface 130 may also prevent guide rod 122 from rolling off of guide rod support 128. Locking pin system 120 may also include cradle assembly 131 for supporting locking pin 121 as it moves between the unlatched position and the latched position. Cradle assembly 131 may include first cradle member 132 and second cradle member 133 each extending from face 134 of frame link 44 to end plate 135. Cradle assembly 131 may also include cradle braces 136 and 137 affixed to face 134 to support first and second cradle members 132 and 133, respectively. In one embodiment, first and second cradle members 132, 133 may form a V-shaped space for locking pin 121. Alternatively, first and second cradle members 132, 133 may form a rectangular, U-shaped, or cylindrical space for locking pin 121. End plate 135 may prevent locking pin 121 from horizontally sliding beyond the ends of first and second cradle members 132 and 133.

Figure 7:
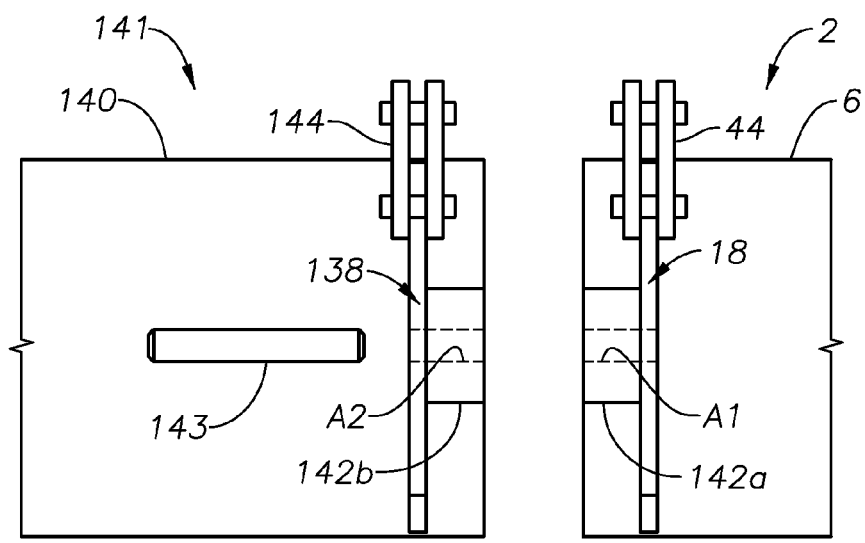
FIG. 7 is a partial side view of a receptacle of a first test cell engaging a receptacle of a second test cell.

FIG. 7 is a side view of the side wall 6 of first test cell 2 containing a first receptacle 18 that engages a second receptacle 138 on a side wall 140 of a second test cell 141. The receptacle 18 comprises the mating block member 142a with aperture A1 therein, and the receptacle 138 comprises the mating block member 142b with aperture A2 therein, and wherein a mating pin 143 joins mating block member 142a with mating block member 142b. In this way, the mating block members 142a, 142b form a mating member from one side wall to another side wall, wherein an operator may connect a series of side walls in series in this manner. The receptacle 18 together with the inserted pin (such as pin 143) through the apertures A1, A2 engage the reciprocal mating block 138 of the side wall 140. In this fashion, multiple test cells may be linked in series depending on the length required for the test equipment. FIG. 7 also depicts the frame link 44 operatively associated with the first test cell 2 along with the frame link 144 operatively associated with the second test cell 141.

Figure 8:
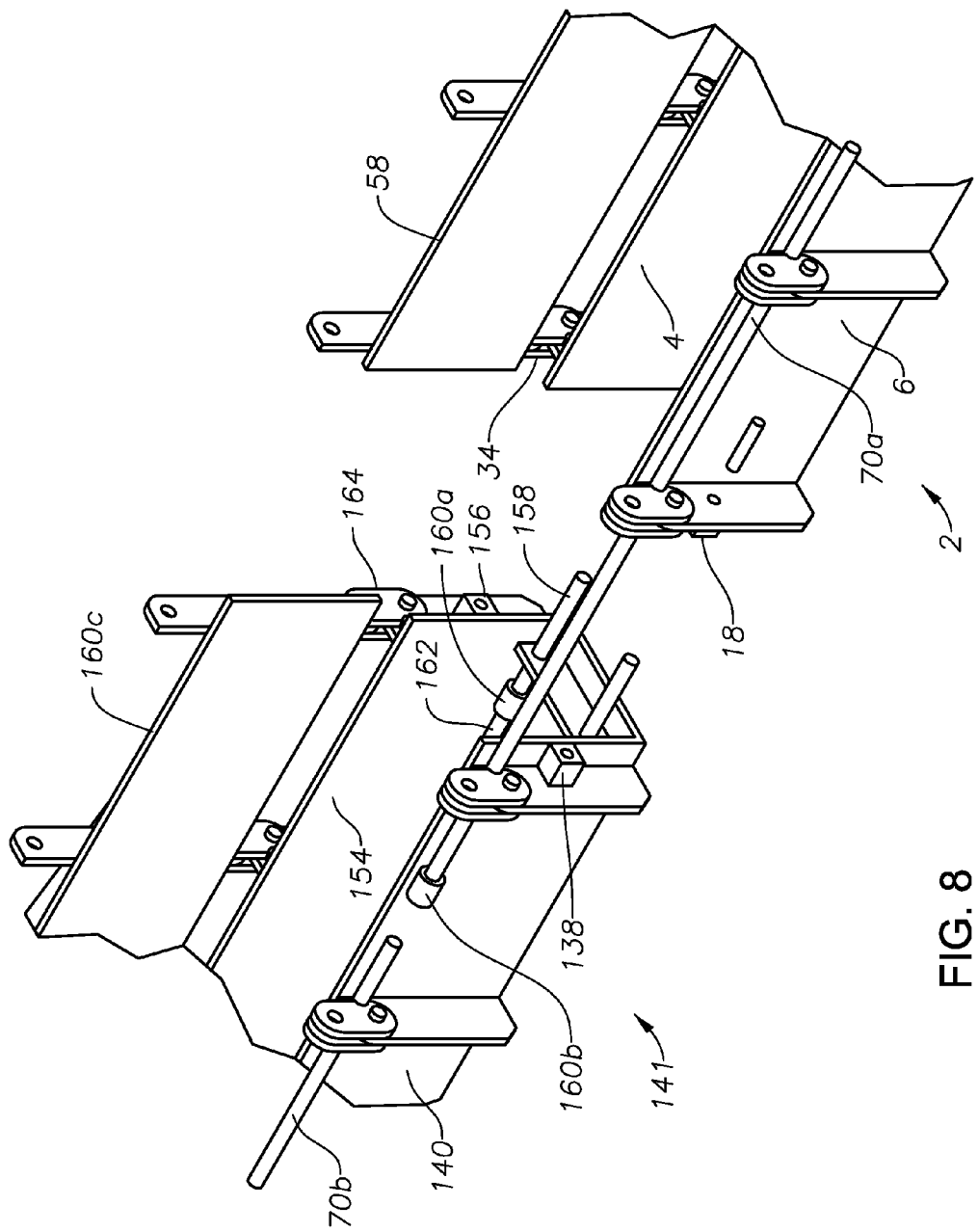
FIG. 8 is a perspective partial side view of a first test cell engaging a second test cell.

FIG. 8 illustrates the interface between the first test cell 2 and second test cell 141, along with some of the tie rods. More specifically, the side wall 4 and the side wall 6 of the first cell 2 are shown, along with the side wall 140 and side wall 154 of the second test cell 141. The view of FIG. 8 shows the receptacle 18 and the receptacle 138 as well as receptacle 156 of the second test cell 141. An inner tie rod 158 is threadedly connected to a coupler 160a, wherein the coupler 160a is connected to the inner tie rod 162. Also, the outer tie rod 70a will be coupled to the outer tie rod 70b via coupler 160b. The pivoting nature of the lid 58 and lid 160c via the frame links 34, 164, respectively, is also shown.

Figure 9:
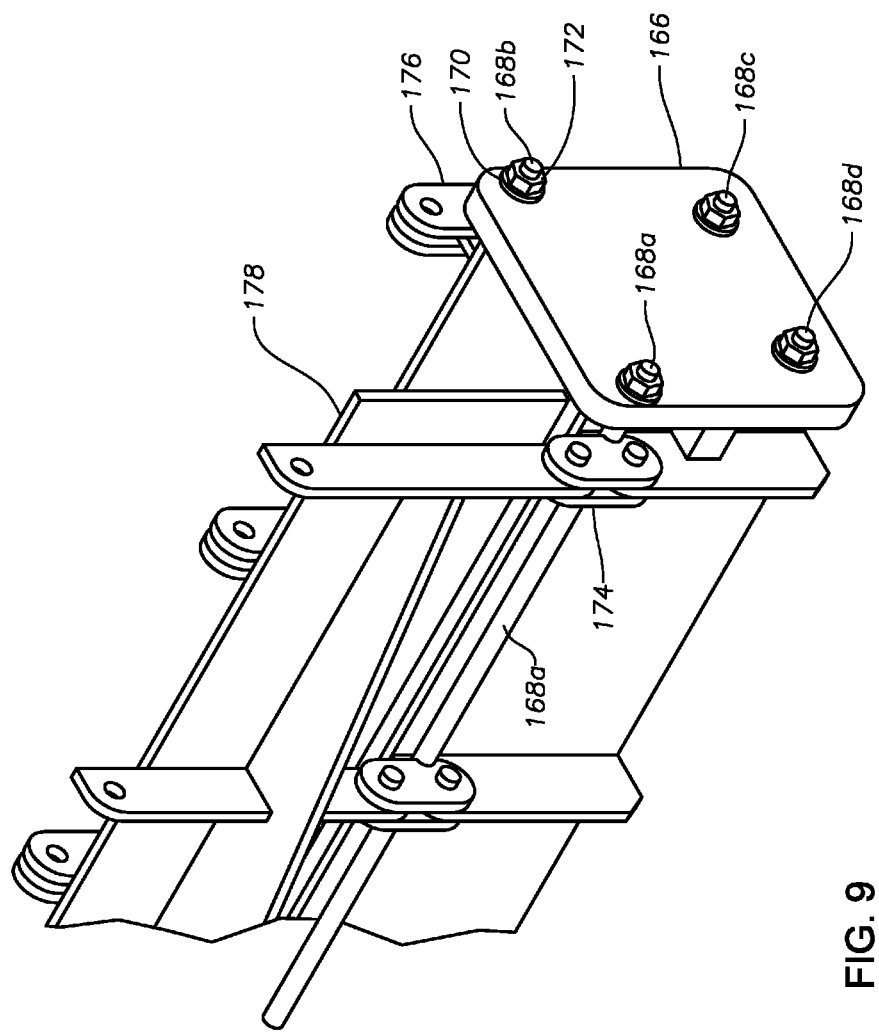
FIG. 9 is a perspective partial side view of a test cell with an impact plate.

FIG. 9 shows one embodiment of an impact plate 166. This view partially depicts the tie rods 168a, 168b, 168c, 168d that extend through openings in the impact plate 166, as previously discussed. The tie rods will be associated with washers and nuts for fastening, as previously noted. For instance, washer 170 is operatively associated with nut 172 for threadedly fastening. FIG. 9 also depicts the pivoting nature of the lid; for instance, the frame links 174, 176 are provided for pivoting and fastening the lid 178.

Figure 10:
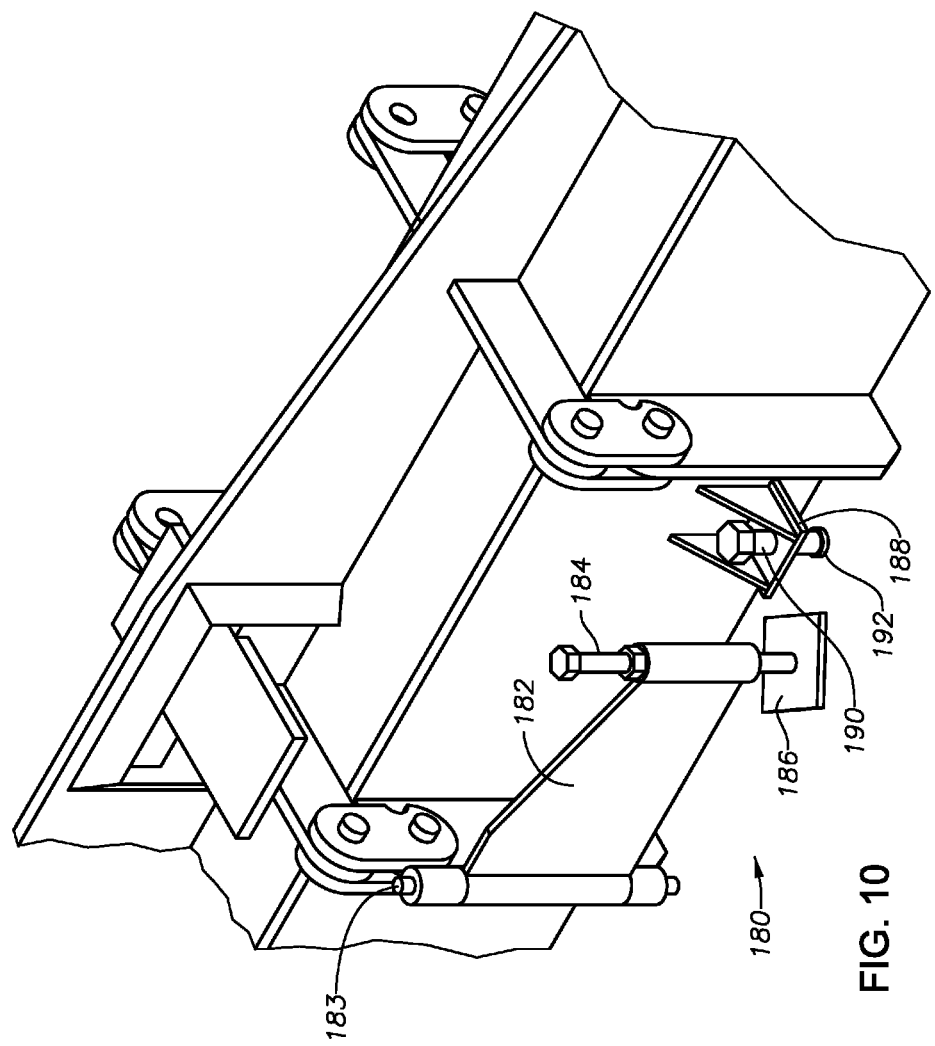
FIG. 10 is a perspective partial side view of one embodiment of the stabilizing means.

FIG. 10 is a view of one embodiment of the stabilizing means 180 for stabilizing the test cell. More specifically, the stabilizing means 180 may includes a rod with pivoting plate 182, and wherein the pivoting plate 182 has a rod 183 on one side and a threaded leg 184 on the other side. The leg 184 can be swung over and then screwed longitudinally within an end of the end plate 182 in order to extend or contract the leg 184 to lift or lower plate foot 186 as needed to provide for stabilization of the test cell. Stabilizing means 180 may be used to prevent the test cell from tipping over when lid 58 is opened as shown in FIG. 1. Additionally, there may also be a leveling bracket 188 connected to the side wall, wherein the leveling bracket 188 has disposed there through a threaded leg 190. The threaded leg 190 also contains a plate foot 192 so that the leg 190 and foot 192 can be raised and lowered to level the test cell. Various types of stabilizing means and leveling members may be employed with the test cell.

FIG. 11 is a schematic illustration of a plurality of test cells in series, including portals and monitoring equipment. FIG. 11 depicts the first test cell 2 connected to a second test cell 200 which in turn is connected to a third test cell 202, wherein the individual test cells 2, 200, and 202 are collectively referred to as test cell unit 204. The impact plate 90 is shown on one end of the test cell 2 and an impact plate 206 is attached to the other end of the test cell 202. It should be noted that test cell 2 and test cell 200 will be interconnected with the receptacle mating block of one test cell engaging the mating block of the other test cell. Also, the test cell 200 will be interconnected to the test cell 202 in a similar fashion i.e. the receptacle mating blocks of one test cell will engage the mating blocks on the wall of the other test cell. And, as previously mentioned, the impact plate 206 will be attached to the test cell 202 through tie rods (as previously described).

As illustrated in FIG. 11, the individual test cells can be continued to be added for the proper length required for the testing of the specific equipment. Specifically, impact plate 206 may be separated from third test cell 202 by disengaging the nut securing each tie rod to impact plate 206. A fourth test cell may be positioned adjacent to third test cell 202, and couplers may be used to extend the tie rods already in place with test cell unit 204 to the fourth test cell (as described above in connection with FIG. 8). Third test cell 202 and the fourth test cell may be guided together as mating pin 143 is inserted through an aperture in a mating block member of third test cell 202 and an aperture in a mating block member of the fourth test cell (as described above in connection with FIG. 7). An impact plate may then also be attached to the free end of the fourth test cell by sliding the impact plate over each of the tie rods and threadedly securing each tie rod to the impact plate with a nut. In one embodiment, impact plate may include a lifting receptacle (e.g., an opening or a pad eye) to facilitate lifting of impact plate by a crane, fork lift, or other lifting device due to the substantial weight of impact plate.

FIG. 11 also illustrates the portal 210 through which lines 212 may be passed from a control unit 214 to the equipment to be tested inside the test cell unit 204. The lines 212 may include hydraulic lines, electric line, electronic sensing lines and pneumatic lines for observing, controlling and monitoring an ongoing pressure test on a piece of equipment. The type of equipment includes, but is not limited to, blowout preventers, tubular members, and bottom hole assemblies. The monitoring equipment will be operatively associated with the control unit 214, and may include cameras, lighting, communication and network devices which can be used by the operator at the work site as well as by the operator located remotely from the work site. Test cell unit 204 may include multiple portals 210. For example, a portal 210 may be included through each end of the side wall of each test cell. If a portal 210 is not used during testing operations, it may be plugged. Alternatively, a portal 210 that is not used during testing operations may remain open to allow for additional venting.

FIG. 12 is a schematic illustration of test cell unit 220 having test cells of varying sizes. The first test cell 222 and second test cell 224 are of similar construction as previously mentioned and wherein an intermediate test cell 226 is also included. The intermediate test cell 226 has an increased width so that a piece of equipment that has three-dimensional shape that could not fit within a rectangular box shape (such as the test unit seen in FIG. 11) would be able to fit inside the test cell unit 220 seen in FIG. 12. All individual cells within this cell unit 220 will have side walls, cell frames and lid braces as previously mentioned. In other embodiments, the test cell unit may include test cells of varying heights or shapes.

An aspect of this disclosure is that impact forces which are created in the event that a piece of equipment fails during testing will be suppressed by the apparatus due to the structure of the disclosed apparatus. The impact forces include the metal (i.e. shrapnel) forces as well as the water (i.e. hydro) forces generated by the sudden release of pressure in the event of equipment testing failure. Another aspect is that the tie rods aid in containing any explosion. Yet another feature is that the apparatus allows for the safety of people in the vicinity of testing in the event of a failure. Also, the force of the water escaping will be significantly limited. Still yet another feature is the suppression of the metal shrapnel released. Still yet another aspect is that in one embodiment the apparatus may be portable. In yet another embodiment, the apparatus is modular and capable of transportability.

Although the present invention has been described in considerable detail with reference to certain preferred versions thereof, other versions are possible. Therefore, the spirit and scope of the appended claims should not be limited to the description of the preferred versions contained herein.

We claim:

1. A pressure test cell for pressure testing equipment, comprising:
a first side wall having an outer surface, an inner surface, a proximal end, and a distal end, a second side wall having an outer surface, an inner surface, a proximal end, and a distal end, and a cell frame operatively associated with the first and second side walls, the cell frame having a first vertical post positioned on the outer surface of the first side wall, a second vertical post positioned on the outer surface of the second side wall opposite the first side wall, and a bottom brace positioned between the inner surfaces of the first and second side walls and between the first and second vertical posts, wherein each of the first and second vertical posts includes an opening;

a lid pivotally mounted on the outer surface of the first side wall;

a first tie rod having a proximal end and a distal end, the first tie rod being disposed through the opening of the first vertical post;

a second tie rod having a proximal end and a distal end, the second tie rod being disposed through the opening of the second vertical post;

a first impact plate including a first aperture and a second aperture, wherein the proximal end of the first tie rod extends through the first aperture and the proximal end of the second tie rod extends through the second aperture for fixation of the first impact plate to the proximal ends of the first and second side walls; and a second impact plate including a first aperture and a second aperture, wherein the distal end of the first tie rod extends through the first aperture of the second impact plate and the distal end of the second tie rod extends through the second aperture of the second impact plate for fixation of the second impact plate to the distal ends of the first and second side walls.

2. The pressure test cell of claim 1, further comprising:
a first frame link having an upper end and a lower end, the lower end of the first frame link being affixed to the first vertical post;
a second frame link having an upper end and a lower end, the lower end of the second frame link being affixed to the second vertical post, the upper end of the second frame link including an opening;
a first lid beam having a first end and second end, the second end of the lid beam including an opening;
a locking system including a first locking pin;
wherein the first end of the first lid beam is pivotally mounted to the upper end of the first frame link;
wherein the lid is operatively attached to the first lid beam; and
wherein with the lid in a closed position, the first locking pin is disposed through the opening in the second end of the first lid beam and the opening in the upper end of the second frame link to secure the lid in the closed position.

3. The pressure test cell of claim 2, further comprising a spar operatively connected to the lid and the first lid beam.

4. The pressure test cell of claim 3, wherein the spar contains a lifting receptacle configured to engage a lifting device for lifting the pressure test cell.

5. The pressure test cell of claim 2, further comprising:
a second cell frame having a first vertical post positioned on the outer surface of the first side wall, a second vertical post positioned on the outer surface of the second side wall opposite the first side wall, and a bottom brace positioned between the inner surfaces of the first and second side walls and between the first and second vertical posts of the second cell frame, wherein each of the vertical posts of the second cell frame includes an opening;
a second lid beam having a first end and a second end, the second end of the second lid beam including an opening;
wherein the first end of the second lid beam is pivotally mounted to the upper end of the first frame link of the second cell frame;
wherein the lid is operatively attached to the second lid beam;
wherein the locking pin system further includes a second locking pin and a guide rod operatively connected to the first and second locking pins;
wherein when the lid is in the closed position and the guide rod actuated to lock the lid in place, the first locking pin is disposed through the opening in the second end of the first lid beam and the opening in the upper end of the second frame link of the first cell frame, and the second locking pin is disposed through the opening in the second end of the second lid beam and the opening in the upper end of the second frame link of the second cell frame.

6. The pressure test cell of claim 1 further comprising a lid opening assembly that includes:
an arm attached to the lid; and
a piston member extending from a cylinder, wherein the piston member is attached to the arm, and wherein the cylinder is attached to the first vertical post.

7. The pressure test cell of claim 1, further comprising a third tie rod having a proximal end and a distal end and a fourth tie rod having a proximal end and a distal end, wherein the bottom brace includes a first opening and a second opening, wherein the third tie rod is disposed through the first opening of the bottom brace and the fourth tie rod is disposed through the second opening of the bottom brace, and wherein the bottom brace is positioned at a base of the pressure test cell.

8. The pressure test cell of claim 7, further comprising a floor structure positioned below the bottom brace, wherein the floor structure interconnects a base of the first side wall and a base of the second side wall.

9. The pressure test cell of claim 8, further comprising a longitudinal brace attached to an internal surface of the floor structure for additional structural support.

10. The pressure test cell of claim 1, further comprising a portal through the first side wall or the second side wall, wherein the portal is configured to allow access by a monitoring equipment to the equipment within the pressure test cell that is undergoing pressure testing.

11. The pressure test cell of claim 1, further comprising a leveling assembly configured to level the pressure test cell relative to a ground surface, the leveling assembly including a leveling bracket affixed to either the first or second side walls, the leveling bracket having disposed therethrough a threaded leg with a plate foot that may be raised or lowered to level the pressure test cell.

12. The pressure test cell of claim 1, further comprising a stabilization assembly configured for stabilizing the pressure test cell relative to a ground surface as the lid is opened and closed, the stabilization assembly including:
a rod affixed to the first or second vertical post;
a pivoting plate having a first end and a second end, the first end of the pivoting plate being operatively connected to the rod; and
a threaded leg operatively connected to the second end of the pivoting plate.

13. The pressure test cell of claim 1, further comprising a first horizontal support beam positioned on the outer surface of the first side wall and a second horizontal support beam positioned on the outer surface of the second side wall for additional structural support.

14. The pressure test cell of claim 1, further comprising a first receptacle attached to the distal end of the first side wall and a second receptacle attached to the distal end of the second side wall for connecting the pressure test cell to a second pressure test cell to form a lengthened pressure testing unit for pressure testing equipment.

15. A variable length pressure testing unit comprising:
a first test cell operatively attached to a second test cell, wherein the first test cell includes:
a first side wall having an outer surface, an inner surface, a proximal end, and a distal end;
a second side wall having an outer surface, an inner surface, a proximal end, and a distal end;
a cell frame having a first vertical post positioned on the outer surface of the first side wall, a second vertical post positioned on the outer surface of the second side wall opposite the first side wall, and a bottom brace positioned between the inner surfaces of the first and second side walls and between the first and second vertical posts of the second test cell, wherein each of the first and second vertical posts of the second test cell includes an opening;
a lid pivotally mounted on the outer surface of the first side wall of the second test cell;
a first tie having a proximal end and a distal end, the first tie rod being disposed through the opening of the first vertical post of the second test cell;
a second tie rod having a proximal end and a distal end, the second tie rod being disposed through the opening of the second vertical post of the second test cell;
an impact plate including a first aperture and a second aperture, wherein the proximal end of the first tie rod of the second test cell extends through the first aperture and the proximal end of the second tie rod of the second test cell extends through the second aperture for fixation of the impact plate to the proximal ends of the first and second side walls of the second test cell;
a first receptacle attached to the distal end of the first side wall;
a second receptacle attached to the distal end of the second side wall; and
wherein the second test cell includes:
a first side wall having an outer surface, an inner surface, a proximal end, and a distal end;
a second side wall having an outer surface, an inner surface, a proximal end, and a distal end;
a cell frame having a first vertical post positioned on the outer surface of the first side wall of the second test cell, a second vertical post positioned on the outer surface of the second side wall opposite the first side wall of the second test cell, and a bottom brace positioned between the inner surfaces of the first and second side walls and between the first and second vertical posts of the second test cell, wherein each of the first and second vertical posts of the second test cell includes an opening;
a lid pivotally mounted on the outer surface of the first side wall of the second test cell;
a first tie rod having a proximal end and a distal end, the first tie rod being disposed through the opening of the first vertical post of the second test cell;
a second tie rod having a proximal end and a distal end, the second tie rod being disposed through the opening of the second vertical post of the second test cell;
an impact plate including a first aperture and a second aperture, wherein the distal end of the first tie rod of the second test cell extends through the first aperture and the distal end of the second tie rod of the second test cell extends through the second aperture for fixation of the impact plate to the distal ends of the first and second side walls of the second test cell;
a first receptacle attached to the proximal end of the first side wall of the second test cell;
a second receptacle attached to the proximal end of the second side wall of the second test cell;
wherein the first receptacles of the first and second test cells are operatively connected together and the second receptacles of the first and second test cells are operatively connected together.

16. The variable length pressure testing unit of claim 15, wherein the first and second receptacles of the first test cell and the first and second receptacle of the second test cell each includes an aperture; wherein a first mating pin engages the aperture of the first receptacle of the first test cell and the aperture of the first receptacle of the second test cell; and wherein a second mating pin engages the aperture of the second receptacle of the first test cell and the aperture of the second receptacle of the second test cell.

17. The variable length pressure testing unit of claim 15, further comprising:
a first coupler connecting the distal end of the first tie rod of the first test cell to the proximal end of the first tie rod of the second test cell; and
a second coupler connecting the distal end of the second tie rod of the first test cell to the proximal end of the second tie rod of the second test cell.

18. The variable length pressure testing unit of claim 15, wherein the first test cell further comprises:
a third tie rod having a proximal end and a distal end;
a fourth tie rod having a proximal end and a distal end; wherein the bottom brace of the first test cell includes a first opening and a second opening, wherein the third tie rod is disposed through the first opening of the bottom brace of the first test cell and the fourth tie rod is disposed through the second opening of the bottom brace of the first test cell; and
wherein the second test cell further comprises:
a third tie rod having a proximal end and a distal end;
a fourth tie rod having a proximal end and a distal end; wherein the bottom brace of the second test cell includes a first opening and a second opening, wherein the third tie rod of the second test cell is disposed through the first opening of the bottom brace of the second test cell and the fourth tie rod of the second test cell is disposed through the second opening of the bottom brace of the second test cell.

19. The variable length pressure testing unit of claim 15, wherein the first test cell further comprises:
a first frame link having an upper end and a lower end, the lower end of the first frame link being affixed to the first vertical post of the first test cell;
a second frame link having an upper end and a lower end, the lower end of the second frame link being affixed to the second vertical post of the first test cell, the upper end of the second frame link including an opening;
a lid beam operatively attached to the lid of the first test cell, the lid beam having a first end and a second end, the second end of the lid beam including an opening, the first end of the lid beam being pivotally mounted to the upper end of the first frame link; and
wherein the second test cell further comprises:

a first frame link having an upper end and a lower end, the lower end of the first frame link of the second test cell being affixed to the first vertical post of the second test cell;

a second frame link having an upper end and a lower end, the lower end of the second frame link of the second test cell being affixed to the second vertical post of the second test cell, the upper end of the second frame link of the second test cell including an opening;

a lid beam operatively attached to the lid of the second test cell, the lid beam of the second test cell having a first end and a second end, the second end of the lid beam of the second test cell including an opening, the first end of the lid beam of the second test cell being pivotally mounted to the upper end of the first frame link of the second test cell.

20. The variable length pressure testing unit of claim 19, wherein the first test cell further comprises a spar operatively connected to the lid and the lid beam of the first test cell; and wherein the second test cell further comprises a spar operatively connected to the lid and the lid beam of the second test cell.

21. The variable length pressure testing unit of claim 15, wherein the first test cell further includes a lid opening assembly comprising:
   an arm attached to the lid of the first test cell; and
   a piston member extending from a cylinder, wherein the piston member is attached to the arm, and wherein the cylinder is attached to the first vertical post of the first test cell; and
wherein the second test cell further includes a lid opening assembly comprising:
   an arm attached to the lid of the second test cell; and
   a piston member extending from a cylinder, wherein the piston member is attached to the arm of the second test cell, and wherein the cylinder is attached to the first vertical post of the second test cell.

\* \* \* \* \*